(12) United States Patent
Brown et al.

(10) Patent No.: US 9,399,100 B2
(45) Date of Patent: Jul. 26, 2016

(54) SHARPS RETRACTION DEVICE

(71) Applicant: C-Major Ltd., Buckinghamshire (GB)

(72) Inventors: Philip Brown, Lancashire (GB); Allen Pearson, Cambridgeshire (GB); James Collins, Cambridgeshire (GB)

(73) Assignee: C-MAJOR LTD. (GB)

( * ) Notice: Subject to any disclaimer, the term of this patent is extended or adjusted under 35 U.S.C. 154(b) by 308 days.

(21) Appl. No.: 14/361,873

(22) PCT Filed: Dec. 6, 2012

(86) PCT No.: PCT/GB2012/053029
§ 371 (c)(1),
(2) Date: May 30, 2014

(87) PCT Pub. No.: WO2013/083979
PCT Pub. Date: Jun. 13, 2013

(65) Prior Publication Data
US 2014/0343506 A1 Nov. 20, 2014

(30) Foreign Application Priority Data

Dec. 6, 2011 (GB) .................................. 1120911.1

(51) Int. Cl.
*A61M 5/32* (2006.01)
*A61M 5/158* (2006.01)

(52) U.S. Cl.
CPC ............. *A61M 5/322* (2013.01); *A61M 5/3232* (2013.01); *A61M 5/3234* (2013.01); *A61M 5/158* (2013.01);
(Continued)

(58) Field of Classification Search
CPC ............. A61M 2005/3227; A61M 2005/3236; A61M 2005/3239; A61M 5/158; A61M 5/322; A61M 5/3232; A61M 5/3234; A61M 5/3272
See application file for complete search history.

(56) References Cited

U.S. PATENT DOCUMENTS 3,572,556 A * 3/1971 Pogacar ................ A61M 5/484
222/309
4,927,414 A 5/1990 Kulli
(Continued)

FOREIGN PATENT DOCUMENTS

EP 0998953 A1 5/2000
WO 0041760 7/2000

OTHER PUBLICATIONS

European Patent Office PCT International Search Report, PCT/GB2012/053029 date of mailing Mar. 15, 2013.
(Continued)

*Primary Examiner* — Rebecca E Eisenberg
(74) *Attorney, Agent, or Firm* — Luedeka Neely Group, PC

(57) ABSTRACT

A medical device comprising an outer housing (400) having a first wall (401) defining a first passage (402) with proximal and distal ends. A retraction housing (412) is slidably received in the first passage (402), the retraction housing (412) having proximal and distal ends and a wall with an interior surface wall defining a helical path (421). Part of the device includes a carriage (422) for releasably receiving a medical sharp (423), the carriage (422) slidably received in the distal end of the retraction housing (412). A latch means (428) is present for retaining the carriage (422) in a first position in the retraction housing (412). A follower (432) is connected to the carriage (422) and engaged with the helical path (421). A stored energy device (434) is connected to the follower (432) and the carriage (422). An actuation means (419) is operable to move the retraction housing (412) towards the distal end of the first passage (402), thereby to release the latch means (428) such that the stored energy device (434) is operable to drive the follower (432) along the helical path (421) and to retract the carriage (422) towards the proximal end of the retraction housing (412).

13 Claims, 16 Drawing Sheets

(52) U.S. Cl.
CPC ...... *A61M 5/3272* (2013.01); *A61M 2005/3227* (2013.01); *A61M 2005/3236* (2013.01); *A61M 2005/3239* (2013.01)

(56) References Cited

U.S. PATENT DOCUMENTS

| | | | | |
|---|---|---|---|---|
| 5,295,965 | A | | 3/1994 | Wilmot |
| 5,643,222 | A | * | 7/1997 | Mahurkar ............ A61B 5/1405 604/195 |
| 6,156,013 | A | * | 12/2000 | Mahurkar ............ A61M 5/322 604/195 |
| 2002/0068907 | A1 | * | 6/2002 | Dysarz ................ A61M 5/3232 604/191 |
| 2004/0204688 | A1 | * | 10/2004 | Lin ..................... A61M 5/3232 604/192 |
| 2005/0087102 | A1 | | 4/2005 | Kuehnle et al. |
| 2009/0306601 | A1 | | 12/2009 | Shaw et al. |
| 2014/0171830 | A1 | * | 6/2014 | Shaw .................. A61M 5/3232 600/576 |

OTHER PUBLICATIONS

European Patent Office PCT International Examination Report, PCT/GB2012/053029 date of mailing Dec. 13, 2013.

* cited by examiner

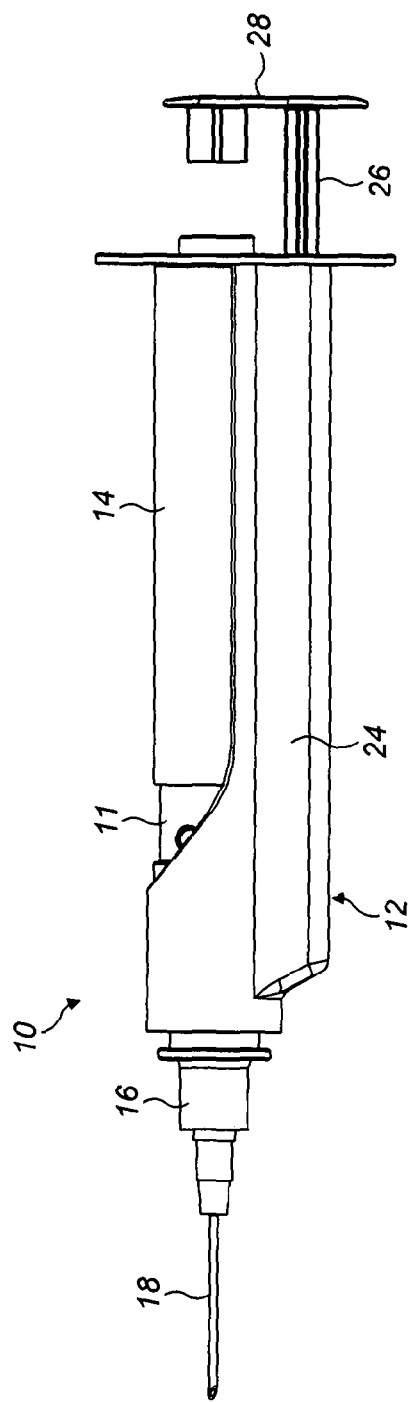
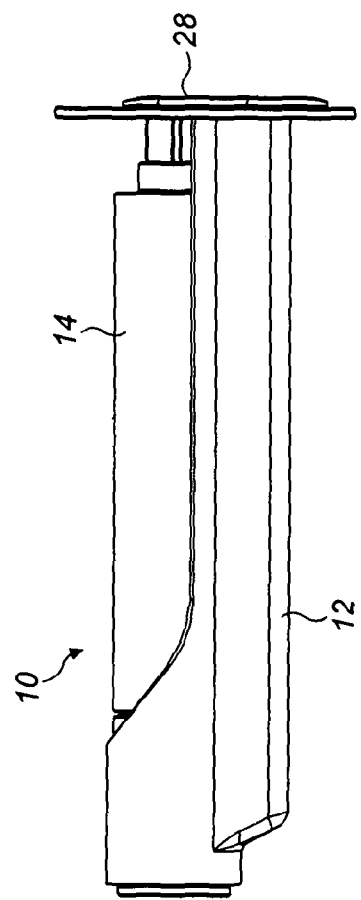

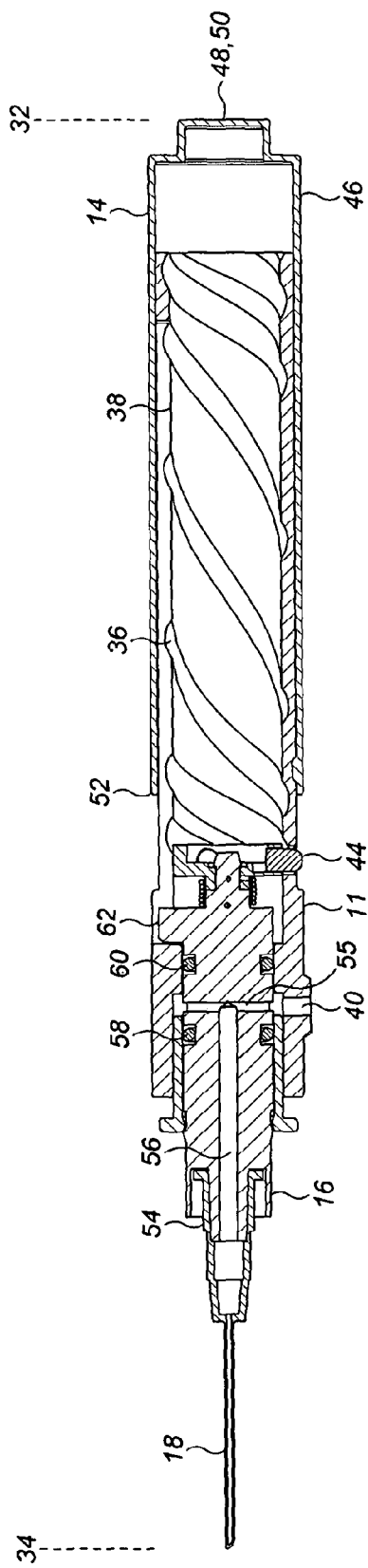
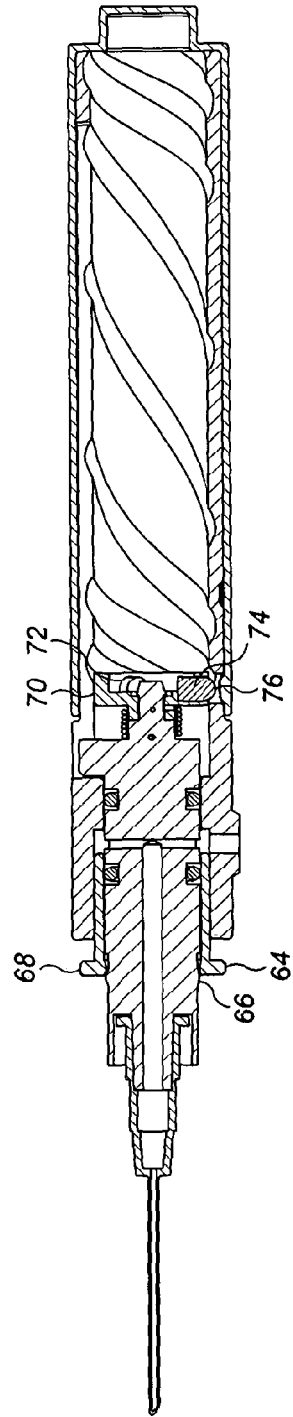
FIG. 2A
FIG. 2B

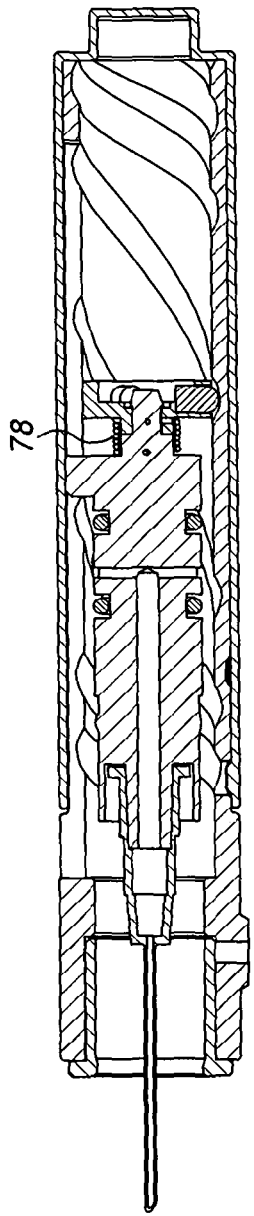
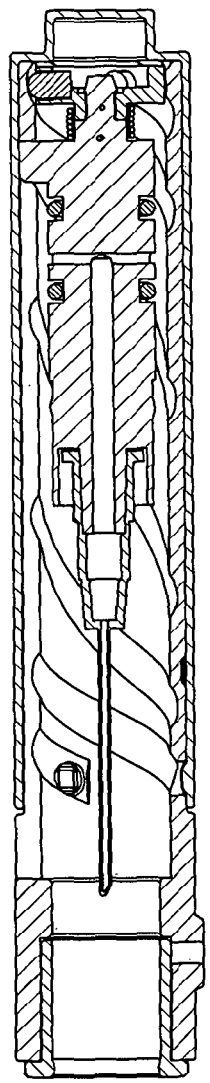
FIG. 2C
FIG. 2D

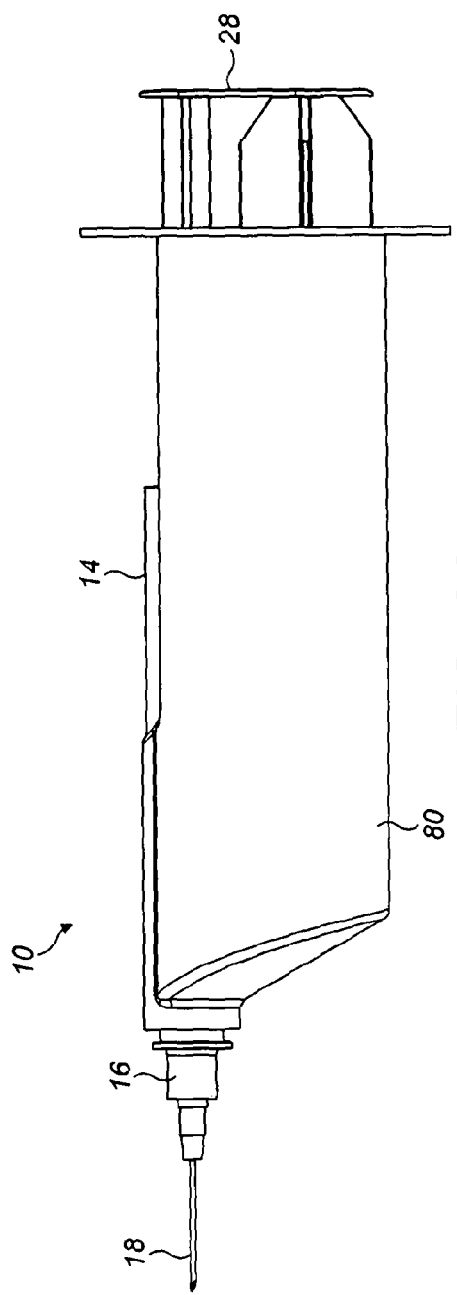
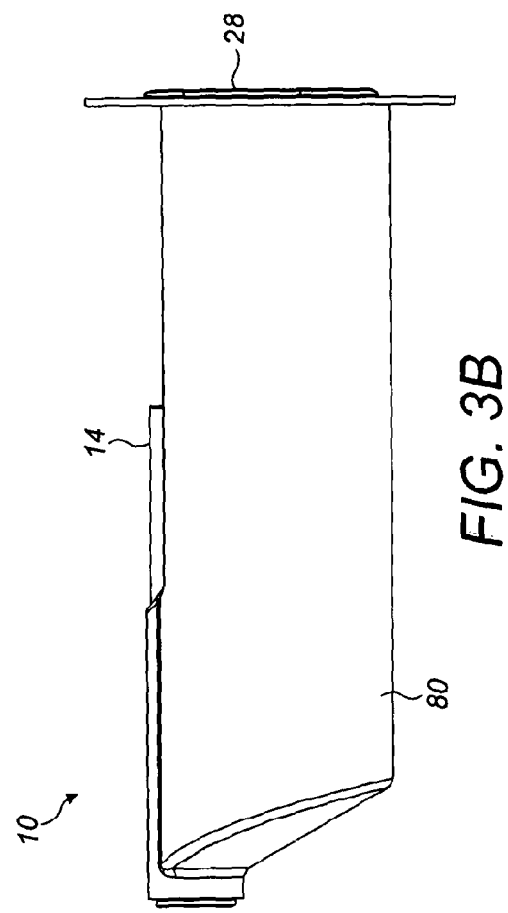
FIG. 3A
FIG. 3B

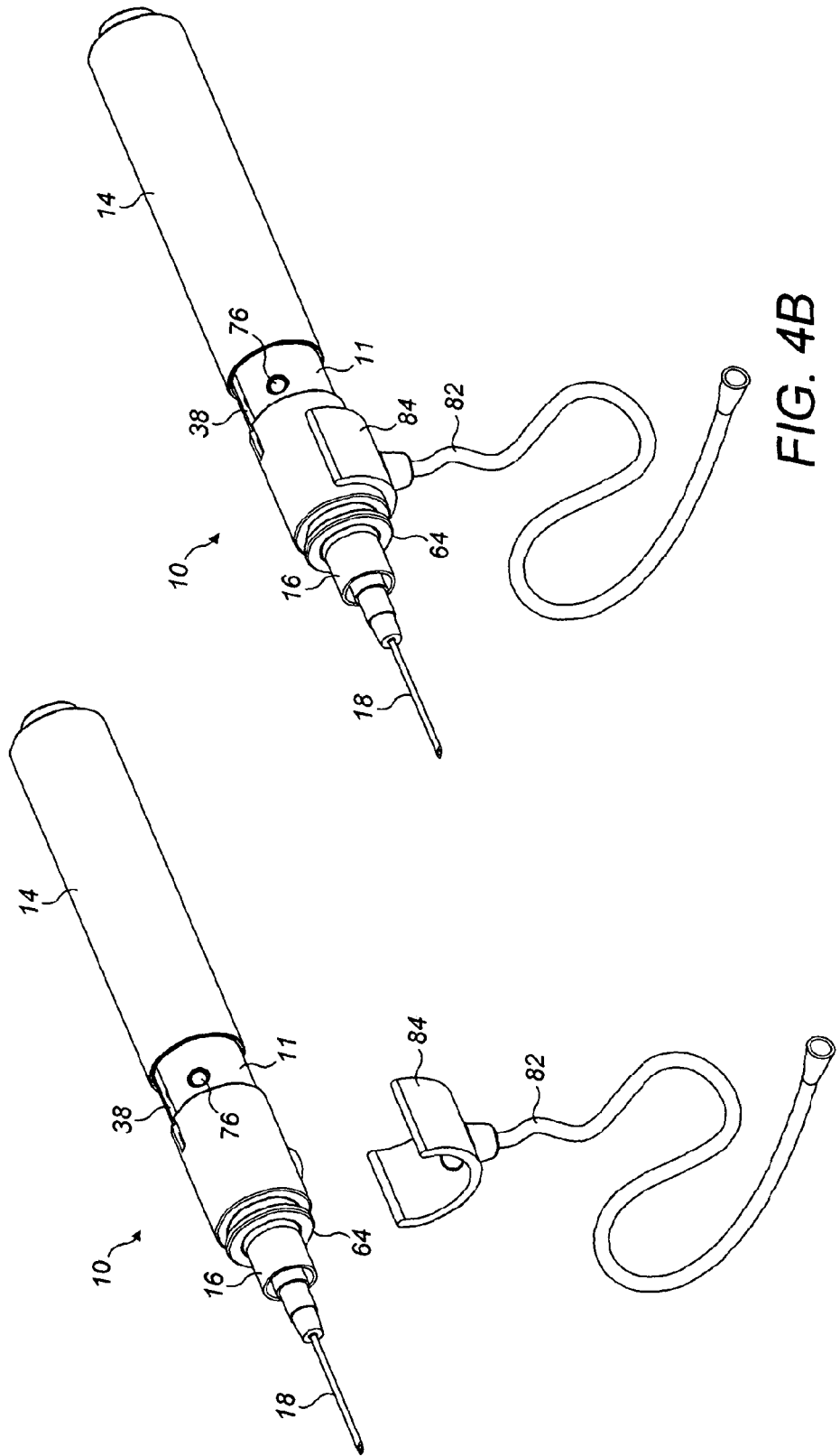

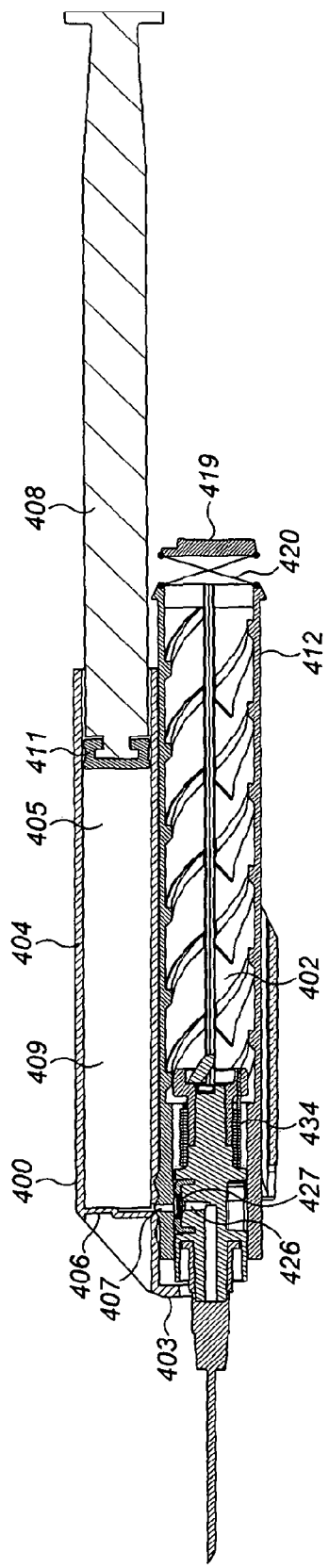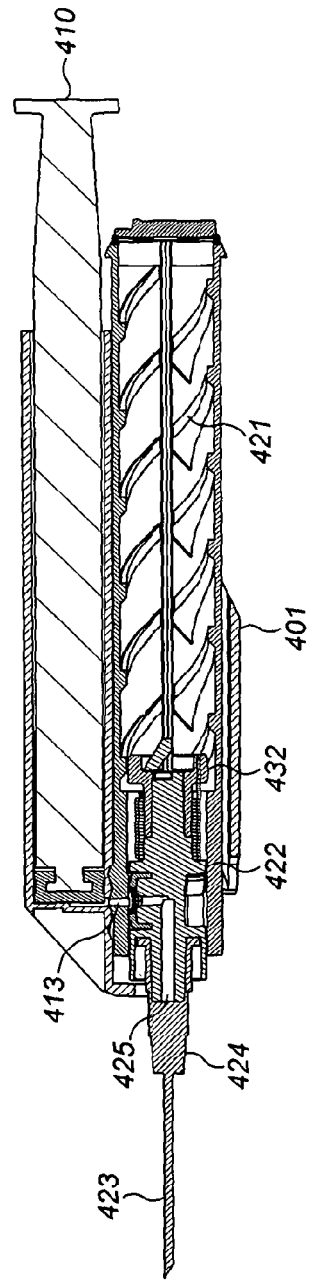
FIG. 9A
FIG. 9B

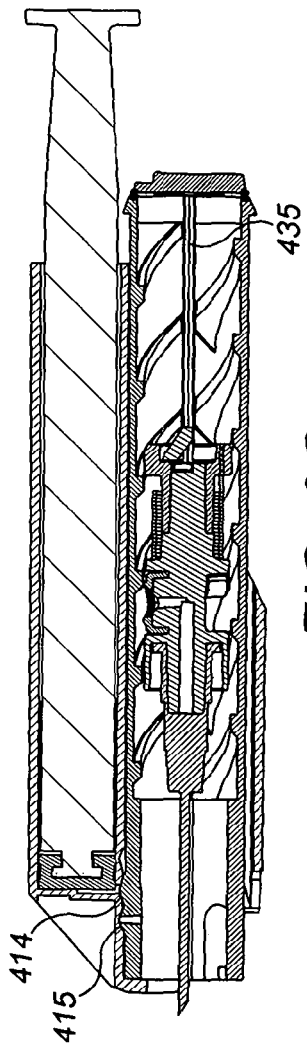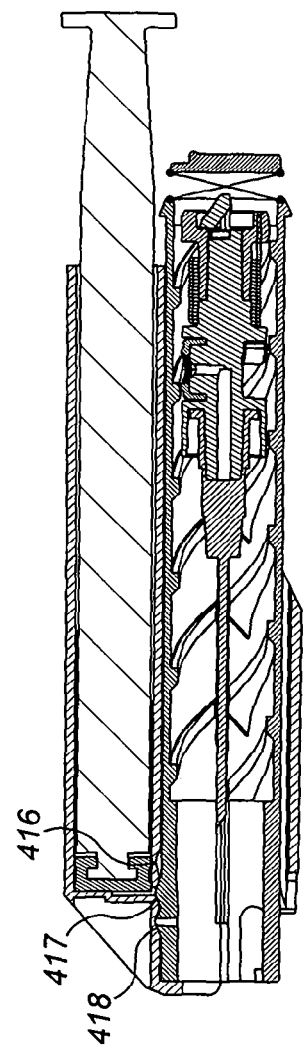

SHARPS RETRACTION DEVICE

CROSS-REFERENCE TO RELATED APPLICATION

This application claims priority under all applicable statutes, and is a U.S. National phase (37 USC Section 371) of International Application PCT/GB2012/053029, filed 6 Dec. 2012, entitled A SHARPS RETRACTION DEVICE, which claims priority to GB 1120911.1, filed 6 Dec. 2011, incorporated herein by reference in their entireties.

The present invention relates to an apparatus for retracting medical sharps after use in medical procedures.

The term "sharps" is well known in the medical field, and is used herein, to mean needles and any other instruments with points, blades, cutting edges etc. which are potentially hazardous.

In the often high pressure conditions of medical and nursing work, the accidental puncture or scratch with a needle, or other sharp object, and the consequent risk of infection with, for example, HIV or hepatitis, is becoming increasingly hazardous to the professions and potentially more costly to health authorities. Therefore there is the need to provide a means for isolating sharps after use such to minimise subsequent injury or infection.

An attempt to address this problem is shown in GB 2341804 which discloses an example mechanism which uses a spring for retracting a needle into the syringe barrel. Numerous other examples are also known.

Other prior art uses complex setups in specific applications to provide retractable needles. These setups however, as well as being fiddly to use, are expensive and therefore unsuitable in the context of single use disposables.

According to the present invention there is provided a device for retaining a medical device comprising an outer housing having a first wall defining a first passage with proximal and distal ends, a retraction housing slidably received in the first passage, the retraction housing having proximal and distal ends and a wall with an interior surface wall defining a helical path, a carriage for releasably receiving a medical sharp, the carriage slidably received in the distal end of the retraction housing, latch means for retaining the carriage in a first position in the retraction housing, a follower connected to the carriage and engaged with the helical path, a stored energy device connected to the follower and the carriage, and actuation means operable to move the retraction housing towards the distal end of the first passage, thereby to release the latch means such that the stored energy device is operable to drive the follower along the helical path and to retract the carriage towards the proximal end of the retraction housing.

Thus the present invention provides a simple device for automatically retracting a sharp after use which has reduced complexity and cost and is simple to operate.

The medical device may further comprise locating means operable to retain the retraction housing relative to the outer housing in a first position and in a second position, wherein the actuation means is operable to move the retraction housing from the first position to the second position.

The locating means may comprise at least one projection on one of the outer housing and the retraction housing and at least two corresponding recesses to receive the projection on the other of the outer housing and the retraction housing.

The medical device may further comprise a latch to retain the carriage in a first position relative to the retraction housing, wherein the actuation means is operable to release the latch such that relative movement between the carriage and the retraction housing is permitted.

The latch may comprise a resilient member on one of the retraction housing and the carriage and biased into engagement with the other of the retraction housing and the carriage when the retraction housing is in its first position relative to the outer housing and wherein the latch is disengaged when the retraction housing is moved into its second position relative to the outer housing.

The outer housing may comprise a stop to limit distal movement of the retraction housing and the carriage in the first passage.

A fluid channel may extend through the carriage from a distal end to a side surface thereof, and the retraction housing wall may comprise a port, wherein when the retraction housing is located in its first position relative to the outer housing, the port in the retraction housing communicates with the fluid channel in the carriage.

In this case, the medical device may further comprise valve means on the carriage to close the fluid channel where it exits the side wall of the sharp connector.

The outer housing may further comprise a second wall defining a second passage adjacent to the first passage, the second passage having a closed distal end and an open proximal end, a port formed through the outer housing adjacent closed distal end of the second passage which communicates with the port in the retraction housing when the retraction housing is in the first position relative to the outer housing, and a plunger slidably received in the second passage to form a chamber for fluid between the plunger and the distal end of the second passage.

When the retraction housing is located in its second position relative to the outer housing, the port in the retraction housing may not communicate with the port in the outer housing; and the wall of the retraction housing may block the port in the outer housing. This way, when the retraction housing is in the second position, any fluid from the chamber is isolated from the port of the retraction housing and thus the first passage.

The stored energy device may comprise spring means.

The follower may be rotatable relative to the carriage and the carriage is precluded from rotation in the retraction housing, such that as the follower is driven along the helical path, the carriage moves axially but does not rotate.

The actuation means may comprise a body connected to the proximal end of the retraction housing by at least one flexible arm.

The invention will now be described in detail, by way of example only, with reference to the accompanying drawings, in which:

FIGS. 1A-1D show views of a medical instrument comprising a sharps retraction device according to a first embodiment of the present invention connected to a fluid dispensing device wherein:

FIG. 1A shows a side view of the medical instrument in an unused state;

FIG. 1B shows a side view of the medical instrument in the used state;

FIG. 1C shows an exploded perspective view of the sharps retraction device and the fluid dispensing device;

FIG. 1D shows a perspective view of the sharps retraction device and the fluid dispensing device as assembled.

FIGS. 2A-2D show cross section views of the sharps retraction device according to the present invention at different stages of its operation.

FIGS. 3A-3D show views of a medical instrument comprising the sharps retraction device according to the present invention connected to an alternative fluid dispensing device wherein:

FIG. 3A shows a side view of the medical instrument in an unused state;

FIG. 3B shows a side view of the medical instrument in the used state;

FIG. 3C shows an exploded perspective view of the sharps retraction device and the alternative fluid dispensing device;

FIG. 3D shows a perspective view of the sharps retraction device and the alternative fluid dispensing device as assembled.

FIGS. 4A and 4B show isometric views of the sharps retraction device according to the present invention when used with alternative ancillary equipment such a connector tube, in both unconnected and connected states respectively.

FIGS. 7A-7D show views of a main housing for use in the further alternative medical instrument of the present invention wherein:

FIG. 7A shows a perspective view of the main housing containing the retraction housing and the carriage in a retracted condition;

FIG. 7B shows a perspective view of the main housing containing the retraction housing and the carriage in an unretracted condition;

FIG. 7C shows a perspective view of the main housing without the retraction housing and the carriage; and FIG. 7D shows a view of the main housing and which shows planes 8-8'; 9-9'; and 10-10'.

FIGS. 9A-9D show cross section views of the further alternative medical instrument at different stages of its operation taken about plane 9-9'.

Figure 1C:
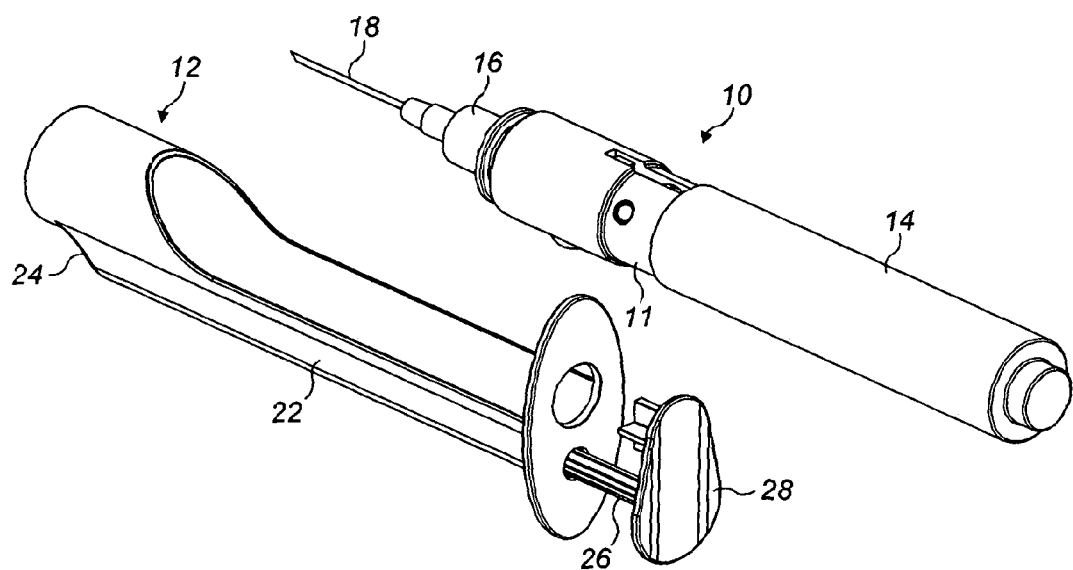
Figure 1D:
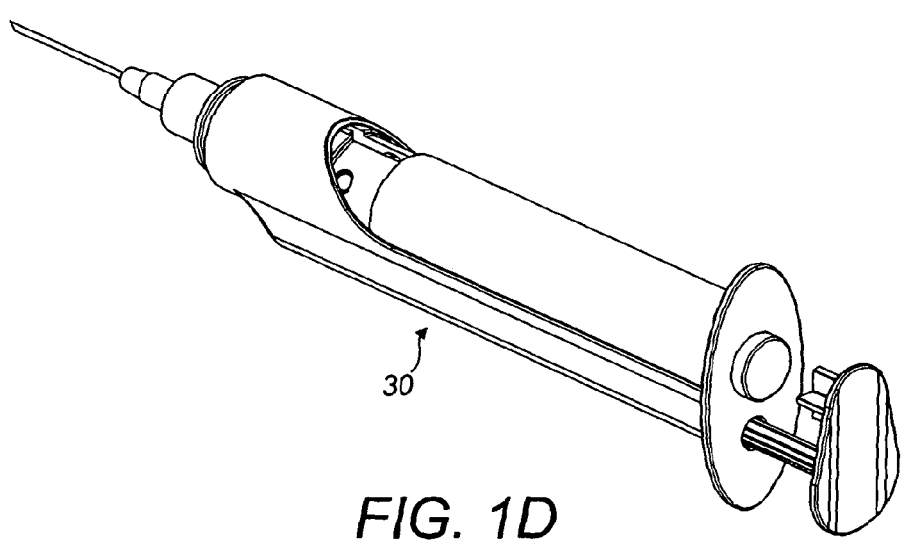

FIGS. 1A-1C show a first embodiment of a sharps retraction device 10 of the present invention in combination with a fluid dispensing device 12. The sharps retraction device 10 includes a casing 11, an actuation mechanism 14, a Luer lock assembly 16 and a sharp 18, in particular a needle. The fluid dispensing device 12 defines a fluid chamber 22, a fluid delivery channel 24 located at the proximal end, and a plunger 26 together with a plunger cap 28. The purpose of the fluid channel 24 is to allow fluid transfer between the fluid chamber 22 and the sharp 18. Although not visible in the figures, for reference purposes, the fluid delivery channel 24 has been shown in FIG. 1C as a dotted line.

Together the sharps retraction device 10 and fluid dispensing device 12 form a syringe 30 for administering medicament to, or withdrawing fluid from, a patient.

In the following description and figures, the distal end shall refer to the end of the retraction device 10 which houses the sharp 18 and is shown in the figures on the left hand side. The proximal end is remote from the sharp 18, and is the end closest to the operator and is on the right hand side in the figures.

FIG. 2A-2D show cross sections of the sharps retraction device 10. The casing 11 of the retraction device 10 is a hollow, generally cylindrical, casing open at both proximal and distal ends. A spiral groove 36 is formed in the inner surface of the proximal portion of the casing 11. The pitch of the spiral groove 36 is varied along the length of the casing 11.

Also inside the cylindrical casing 11 is an anti rotation feature 38 which comprises an axial slot which extends between the proximal and distal ends of the casing 11 but not along its full length.

A radial side channel 40 near the distal end 34 of the casing 11 forms an opening into the interior of the casing 11. A further opening 44 passes through the casing 11 at the distal end of the spiral groove 36.

A hollow retraction sleeve 46 is slidably received over the proximal end of the casing 11. The retraction sleeve 46 comprises a closed proximal end 48, thus forming an actuation surface 50. The distal end 52 of the retraction sleeve 46 is open to receive the casing 11.

The Luer lock assembly 16 is slidably received in the distal end 34 of the casing 11. The Luer lock assembly 16 has at its distal end a standard Luer lock connector 54 to receive a hollow needle or other medical sharp. The Luer lock assembly 16 contains a radial channel 55 and an axial channel 56. When the Luer lock assembly 16 is mounted in the casing 11, the channels 55 and 56 form a fluid path which connects the casing side channel 40 with the needle. O-rings 58; 60 isolate the fluid path 56 to prevent fluid leakage into the casing 11.

Toward the proximal end of the assembly 16 is a radially protruding shoulder 62 which is configured to sit in the slot of the anti rotation feature 38.

Inside the distal end of the casing 11 and surrounding part of the Luer lock assembly 16 is a circumferential collar 64, which is held in place by a raised ridge 66 formed on the Luer lock assembly 16. The collar 64 comprises a rim 68 at its distal end, which extends radially outwardly.

A retraction rate controller 70 is located at the proximal end of the Luer lock assembly 16. The controller 70 is essentially a disc rotatably mounted on a shaft protruding from the proximal end of the casing 11. The controller 70 has at its proximal end a pin 72 for engagement with the spiral groove 36 of the casing 11. A rotation lock 74, with head 76, is connected to the retraction rate controller 70. The lock 74 is movable radially and biased outwardly so that initially it locates in opening 44, thereby preventing rotation of the controller 70.

Connecting the Luer lock assembly 16 to retraction rate controller 70 is a torsion spring 78. The spring 78 connects to the proximal face of the Luer lock assembly 16 and also to the distal face of the retraction rate controller 70. The spring 78 is held in torsion by the lock 74, which is initially located in opening 44.

In a starting position of the sharps retraction device 10, the Luer lock assembly 16 rests at the distal end of casing 11 as shown in FIG. 2A, locked in place by the engagement of rotation lock 74 in the opening 44. A sharp 18 such as a needle as shown may be attached to the standard Luer lock connector by medical personnel when required. In this position, the head 76 of the rotation lock 74 extends beyond the outer diameter of the casing 11. By pushing the retraction sleeve 46 towards the distal end of the retraction device 10, the sleeve 46 comes into contact with the head 76 of the rotation lock 74, causing the rotation lock 74 to be depressed radially inwardly inside the casing 11, as shown in FIG. 2B. Once the rotation lock 74 is depressed radially inwardly, the tension in torsion spring 78 is released, causing the retraction rate controller 70 to rotate. As pin 72 engages in groove 36, rotation of controller 70 causes pin 72 to travel along the spiral groove 36 towards the proximal end of the casing 11, as shown in FIG. 2C.

Movement of the retraction rate controller 70 along the spiral groove 36 also causes the entire Luer lock assembly 16 to move, due to the physical connection of the Luer lock assembly 16 with the retraction rate controller 70. As the Luer lock assembly 16 retracts, it does not rotate. Instead, the Luer lock assembly 16 is guided without rotation towards the proximal end of the casing 11 by engagement of shoulder 62 in the slot of the anti rotation feature 38. As the Luer lock assembly 16 is connected to the sharp 18, the retraction of the Luer lock assembly 16 also causes the sharp 18 to be retracted into the casing 11.

Progression of the Luer lock assembly 16 and retraction rate controller 70 towards the proximal end of casing 11 continues until either the tension in torsion spring 78 is relieved (due to the relative twisting motion of the retraction rate controller with the Luer lock assembly), or until the shoulder 62 has progressed along the total length of the anti rotation feature 38. As shown in FIG. 2D, the retraction range must be enough to ensure that the sharp 18 is completely within the casing 11.

The retraction rate of the Luer-lock assembly 16 into the casing 11 is controlled by the interaction between the pin 72 of the retraction rate controller 70 and the spiral groove 36. During the retraction motion, the pin 72 is forced to follow the profile dictated by the spiral groove 36. In situations where a rapid retraction rate is required, a pitch L of the spiral 36 may be made large. Conversely, in situations where a slower retraction rate is required, the pitch L of spiral 36 may be decreased. By varying the pitch L over the working range of the retraction device 10, a retraction rate withdrawal profile can be generated, wherein the retraction rate of the Luer lock assembly 16 can vary depending on its position along the spiral 36.

By being able to control the retraction speed of the Luer lock assembly 16, this allows better control over how the sharp 18 is removed from a patient. Specifically, by reducing jerk in the sharp's removal, this eliminates spluttering, that is the escape of fluid from the sharp during its retraction and minimises the risk of injury to the patient caused by the sharp's removal.

In use, the fluid dispensing device 12 is connected to the sharps retraction device 10 to create a syringe 30 by passing the proximal end of the sharps retraction device 10 through the distal end of the fluid dispensing device 12. A suitable snap fit between the two devices causes them to lock together in a piggy back style arrangement, as shown in FIGS. 1A-1D. In the located position, the side channels 24; 40 from both devices 12; 10 communicate to form a passage for fluid transfer between the fluid chamber 22 and the sharp 18. Further, in the located position, the plunger cap 28 from plunger 26 overlaps with the actuation surface 50 at the distal end of sleeve 46.

To administer fluid from the fluid chamber 22 to the sharp 18, initially the plunger 26 is positioned in an extended proximal position, as shown in FIG. 1A. On depression of the plunger 26 towards the distal end of the fluid dispensing device 12, fluid in the fluid chamber 22 is forced through the connected passages 24; 40; 55; 56 into the sharp 18.

Towards end of plunger stroke, the overlapping portion of plunger cap 28 comes into contact with the actuation surface 50. Continued depression of the plunger 26 causes movement of the retraction sleeve 46 in the distal direction over casing 11 and ultimately causes release of the rotation lock 74 and retraction of the Luer lock assembly 16 as detailed above.

To prevent further fluid escape from the fluid chamber 22 and channel 24 after retraction, the collar 64 is provided to block side channel 40.

In use, as the Luer lock assembly 16 is retracted into the casing 11, the ridge 66 formed on the Luer lock assembly 16 comes into contact with the collar 64. This forces the collar 64 to move proximally together with the Luer lock assembly 16. The collar 64 moves with the Luer lock assembly 16 until the rim 68 comes into contact with casing 11. Once the rim 68 abuts the casing 11 the collar 64 seals off passage 40 to prevent any remaining fluid from escaping from channel 24 and chamber 22. Once the collar 64 has abutted casing 11, the ridge 66, forced by the restoring force in the spring 78, deforms underneath rim 68. Having deformed round rim 68, the Luer lock assembly 16 then continues to move unobstructed into the retraction casing 11.

In some applications, a user may wish to retract the Luer lock assembly 16 before the plunger 26 has proceeded fully through its working range to contact actuation surface 50. Alternatively, in situations where the instrument is used for aspiration as opposed to injection, as the plunger 26 is pulled proximally it will never engage with the actuation surface 50. In these cases, a separate means to initiate retraction of the Luer lock assembly 16 and sharp 18 is required. In this case, the retraction device 10 may be designed to allow manual engagement of the rotation lock 74 by the user such to trigger the retraction motion.

It will be seen that the advantage of the above setup is that it allows sharps to be isolated after use. This helps to minimise any subsequent injury or infection caused by exposed sharps. Furthermore, by controlling how the sharp is retracted using a helical path, fluid escape during retraction of any sharp can be eliminated.

Figure 3C:
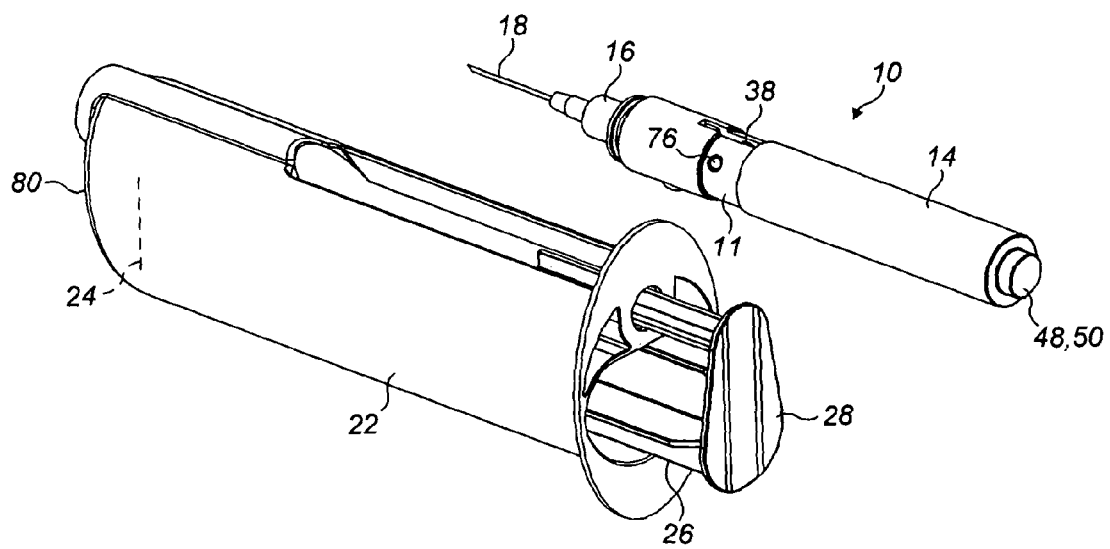
Figure 3D:
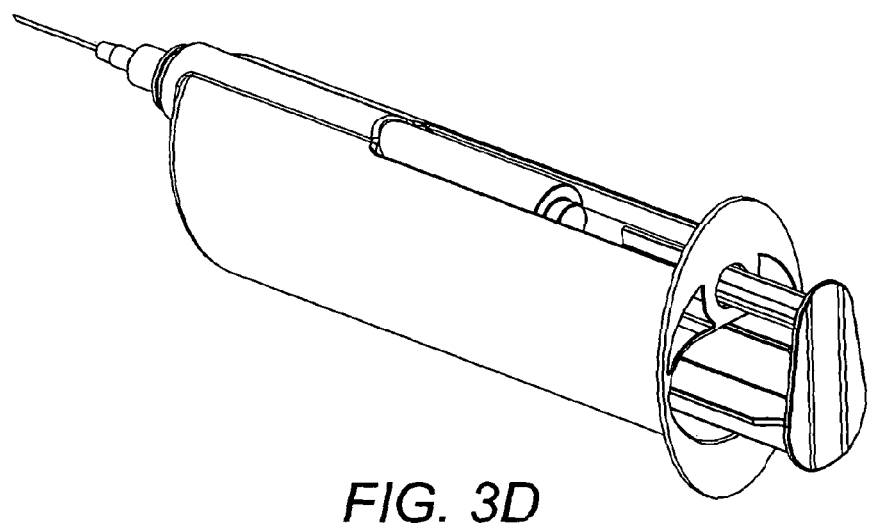

FIGS. 3A-3C show an alternative fluid dispensing device 80, comprising a larger fluid chamber 22. It will be appreciated therefore that the same retraction device 10 can be combined with different fluid dispensing devices 12; 80 to provide syringes 30 for delivering different amounts of medicament.

In any of the fluid dispensing devices 12; 80, it is apparent that the device need not be opaque. In some instances, the fluid dispensing device 12; 80 may be transparent to allow viewing of the fluid chamber 22 located in the device. Markings may be also present on the device so as to allow volumetric measurement of the fluid located inside the fluid chamber 22.

As shown in FIGS. 4A and 4B, in other embodiments the retraction device 10 may be connected to ancillary equipment other than a fluid dispensing device 12; 80. For example, a detachable connector tube 82 may be provided. This configuration may be used in situations where the retraction device 10 is used for aspiration, as opposed to injection. Alternatively, this setup may be used where fluid is required to be delivered or extracted by a medical machine, for example a dialysis machine. The tube 82 comprises two ends, the first end being suitable for attachment to the retraction device 10 and the second end suitable for attachment to medical fluid containers or delivery systems. A guide collar 84 is located at the first end of the tube 82. The collar 84 attaches with the retraction device 10 e.g. by snap fit engagement around casing 11, to provide a sealed fluid connection between the tube 82 and the side channel 40 of the retraction device 10, as shown in FIG. 4B. Any suitable connection means may be provided at the second end of the tube to allow connection of the tube with any medical fluid containers or delivery systems. Fluid may be delivered to the needle 18 via the tube 82, or fluid may be withdrawn from the patient through the needle 18 and passed into the tube 82. Thereafter, the retraction device 14 may be operated, for example by manual pressure on the actuation surface 50, to retract the needle 18 and the Luer lock assembly 16 in the casing 11.

Another embodiment of the present invention is shown in FIGS. 5A to 10D.

The medical device shown in these Figures is formed of three main parts, a main housing 400 a retraction housing 412 and a retractable carriage 422.

The main housing 400 comprises a first curved wall 401 defining a first cylindrical passage 402 with a longitudinal axis and proximal and distal ends. This may be best seen in FIGS. 7A-7D and 9A-9D. In the orientation illustrated in the Figures, the proximal end is on the right hand side and the distal end on the left hand side.

At least part of the first curved wall 401 may describe a full circle such that it is O-shaped in cross section. Alternatively, the first curved wall 401 could be partly cut away so that it is substantially C-shaped in cross section. The first curved wall 401 is substantially open at its proximal and distal ends. However, at the distal end a lip 403 extends radially inwardly a short distance.

In this example, the main housing 400 further comprises a second curved wall 404 integral with the first curved wall 401 and defining a second cylindrical passage 405 parallel and adjacent to the first cylindrical passage 402. The second cylindrical passage 405 has an open proximal end but is closed at its distal end by a distal end wall 406. Adjacent the distal end wall 406 a passage 407 is formed through the integral first and second curved walls 401, 404 to connect the first and second cylindrical passages 402, 405 together. This is best seen in the enlarged cross sections in FIGS. 8A and 8B.

A plunger 408 is slidably received in the second cylindrical passage 405 and is moveable axially to form a chamber 409 in the distal end of the second cylindrical passage 405 (see FIG. 9A). The plunger 408 comprises a plunger cap 410 at its proximal end and a head with a fluid seal 411 at its distal end. Thus, a chamber 409 for receiving fluid is formed in the second cylindrical passage 405 between the distal end wall 406 and the head 411 of the plunger 408.

Figure 6A:
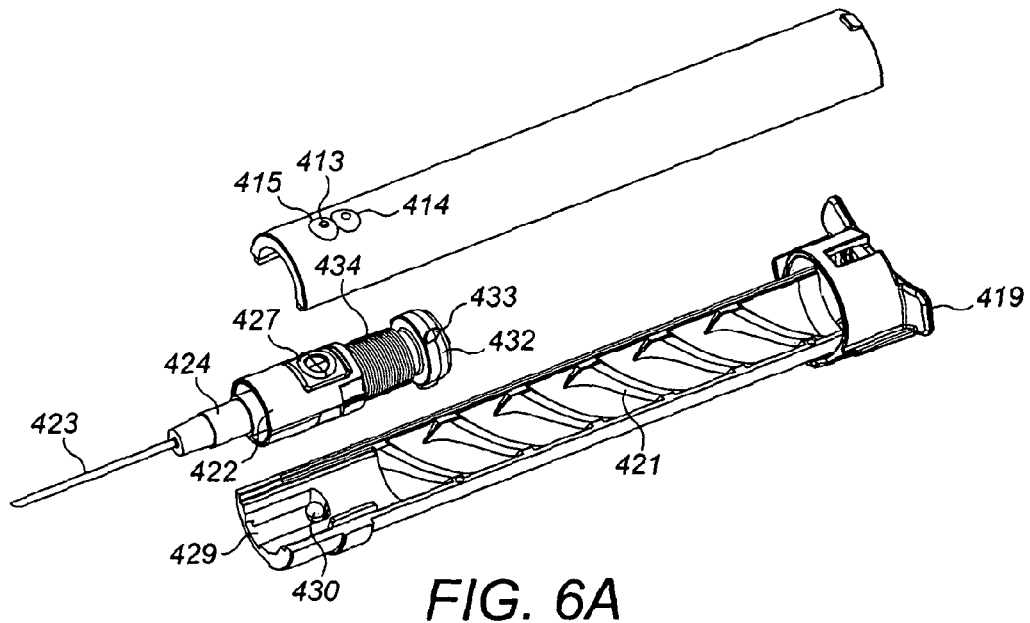
FIGS. 6A-6C show perspective views of the carriage from FIGS. 5A and 5B contained within a retraction housing for use in the further alternative medical instrument of the present invention.
Figure 6B:
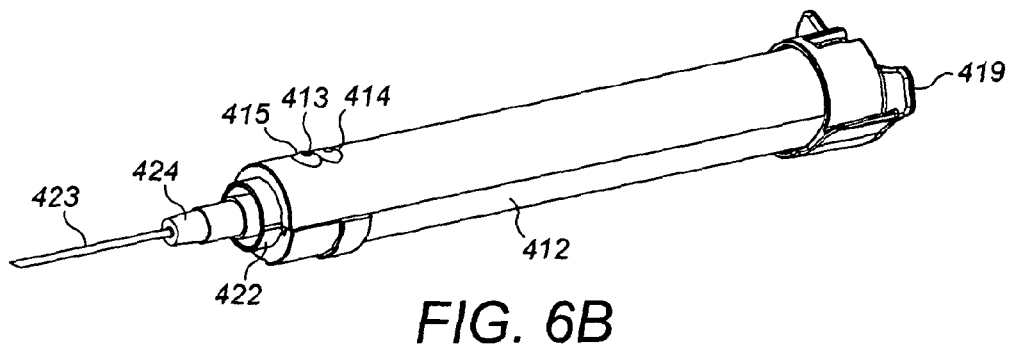
Figure 6C:
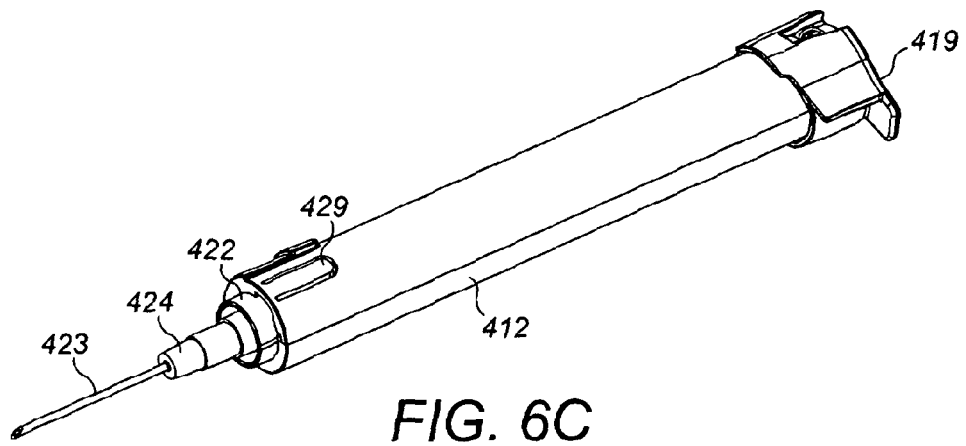
Figure 7A:
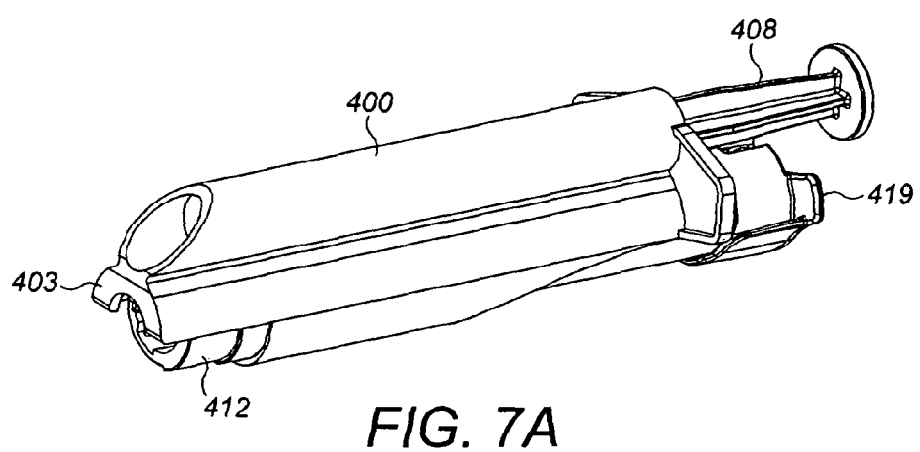
Figure 7B:
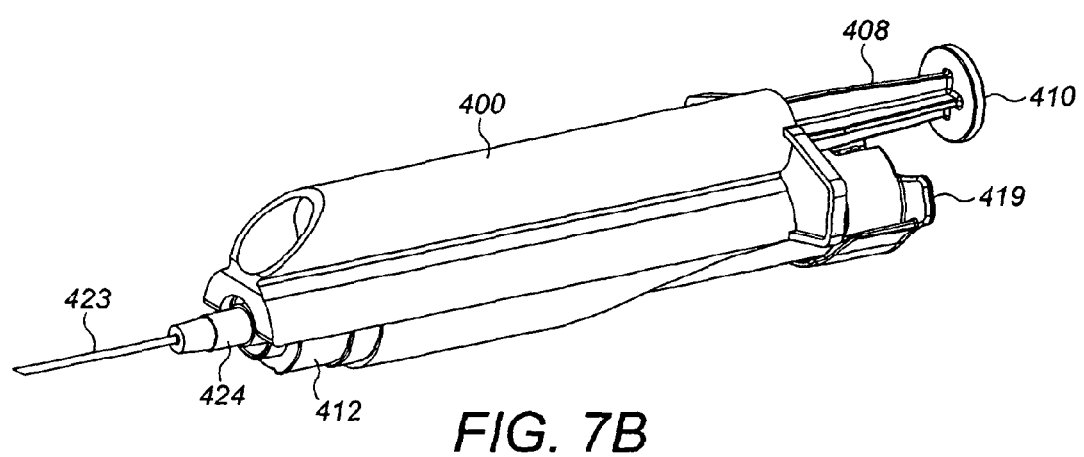
Figure 7C:
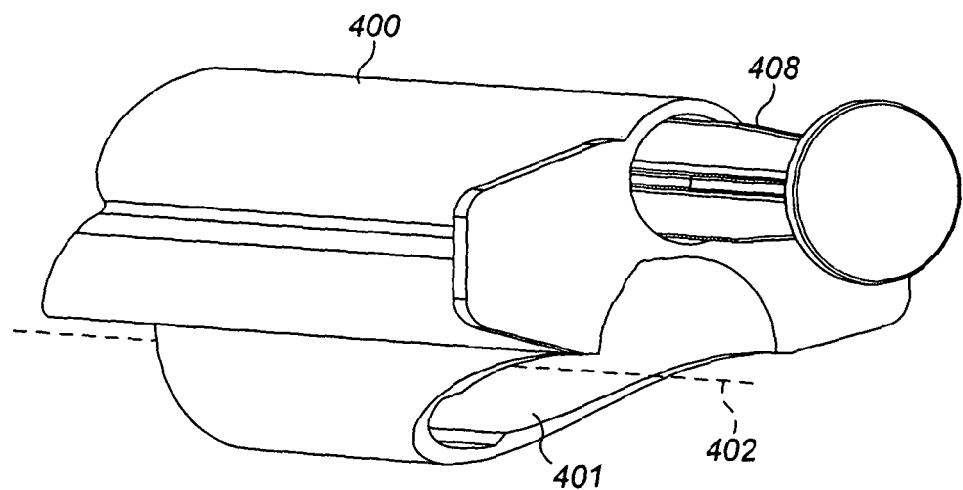
Figure 7D:
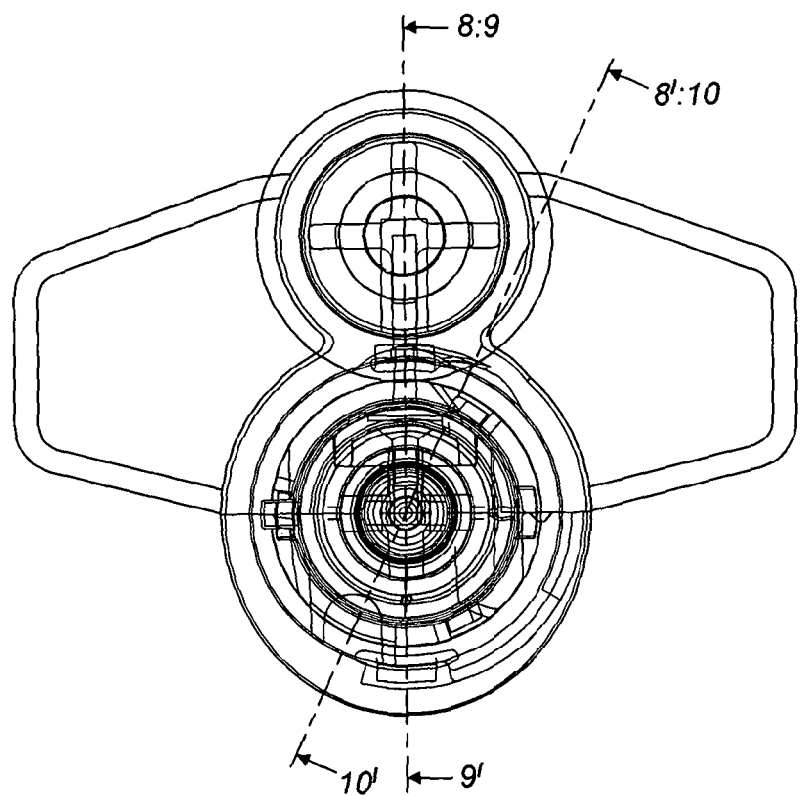

The retraction housing 412 best seen in FIGS. 6A-6C comprises a hollow cylinder. For convenience, this may be manufactured in two parts which fit together as shown in FIG. 6A. The retraction housing 412 is slidably received in the first passage 402 from the proximal end. The lip 403 formed on the first curved wall 401 of the main housing 400 acts as a stop to limit movement of the retraction housing 412 in the first cylindrical passage 402 so that the retraction housing 412 cannot protrude from the distal end of the first cylindrical passage 402.

Figure 8A:
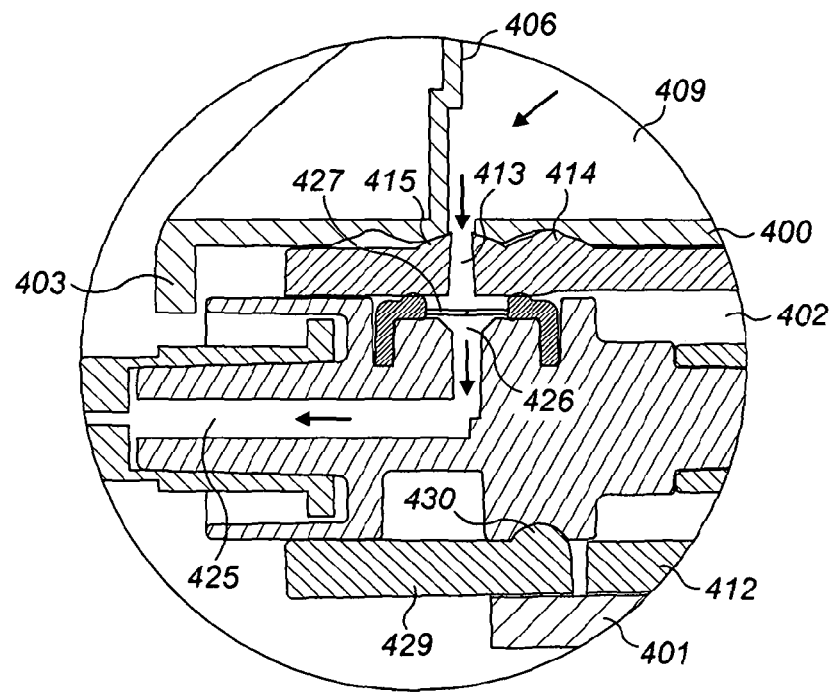
FIGS. 8A-8B show enlarged cross section views of the distal end of the further alternative medical instrument at different stages of its operation, based on plane 8-8'.

A passage 413 is formed through the wall of the retraction housing 412 which can be aligned with the passage 407 in the main housing 400 to connect the fluid chamber 409 in the second cylindrical passage 405 with the interior of the retraction housing 412 (see FIG. 8A).

The main housing 400 and the retraction housing 412 are provided with a locating means to releasably locate them in two relative positions. In this example, a pair of projections 414, 415 are formed on the outer surface of the retraction housing 412 close to its distal end. These may be of any convenient form but here are circular domed or conical projections. Three correspondingly shaped recesses 416, 417, 418 are formed in the interior surface of the first curved wall 401 of the main housing 400.

Figure 8B:
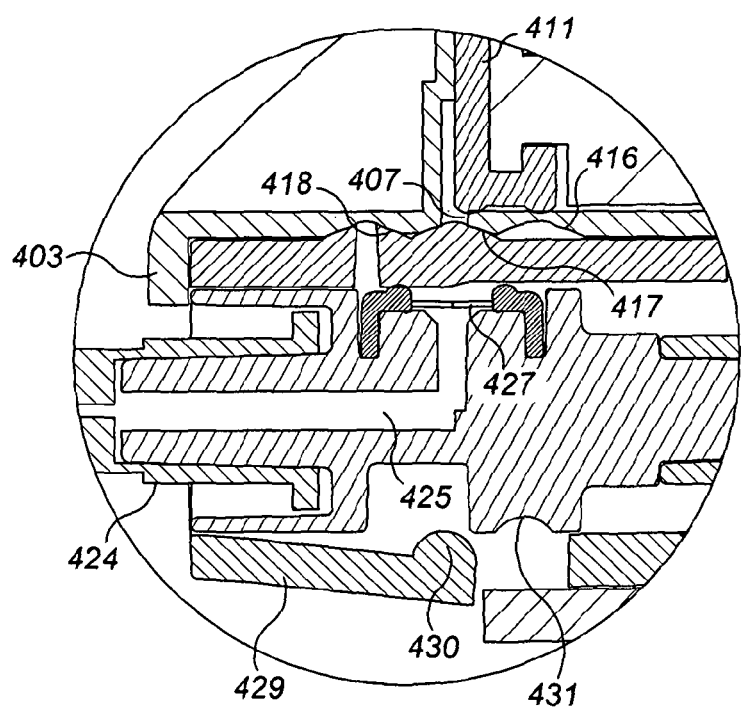

As shown in FIGS. 8A and 8B, the passage 413 through the wall of the retraction housing 412 passes through the distal projection 415. The passage 407 through the wall of the main housing 400 passes through the middle one 417 of the three recesses. In a first position of the retraction housing 412 relative to the main housing 400, the distal projection 415 is received in the middle recess 417 and the proximal projection 414 is received in the proximal recess 416. The two passages 407, 413 are aligned as in FIG. 8A.

To move to a second position of the retraction housing 412 relative to the main housing 400, pressure is applied to the proximal end of the retraction housing 412. When sufficient pressure is applied the resistance provided by the engagement of the projections and recesses of the locating means is overcome and the retraction housing 412 moves distally until the distal projection 415 engages instead with the distal recess 418, and the proximal projection 414 engages with the middle recess 417. The passage 407 in the main housing 400 is now closed by the distal projection 415 as shown in FIG. 8B.

In order to facilitate application of pressure to the retraction housing 412 to move it from the first to the second position, actuating means are provided at its proximal end. This may simply be a proximal end wall closing the retraction housing 412 and providing a surface for a user to push against. However, in this embodiment the actuation means comprises a cap or body 419 connected to and slightly spaced from the proximal end of the retraction housing 412 by at least one, and preferably two, flexible arms 420. In this way, pressure must be applied first to move the body 419 from its spaced position (FIG. 9A) into contact with the retraction housing 412 (FIG. 9B). Further pressure applied will push the retraction housing 412 distally in the first passage 402. Thus, the flexible arms 420 help avoid any unintentional movement of the retraction housing 412 because slight or accidental pressure on the actuating means will only move it towards the retraction housing 412 and increased, more sustained pressure is required to move the entire retraction housing 412.

The inner surface of the retraction housing 412 is formed with a helical pathway 421. This may be formed as a groove recessed into the wall, or a projection extending from the wall. The helical path 421 may be continuous or intermittent. It extends from the proximal end more than halfway along the retraction housing 412 towards the distal end. The helical pathway 421 may consist of turns of a single helix but preferably it consists of turns of three helices.

The distal end of the retraction housing 412 is open and slidably receives a carriage 422 for releasably connecting to a needle 423 or other medical sharp.

Figure 5A:
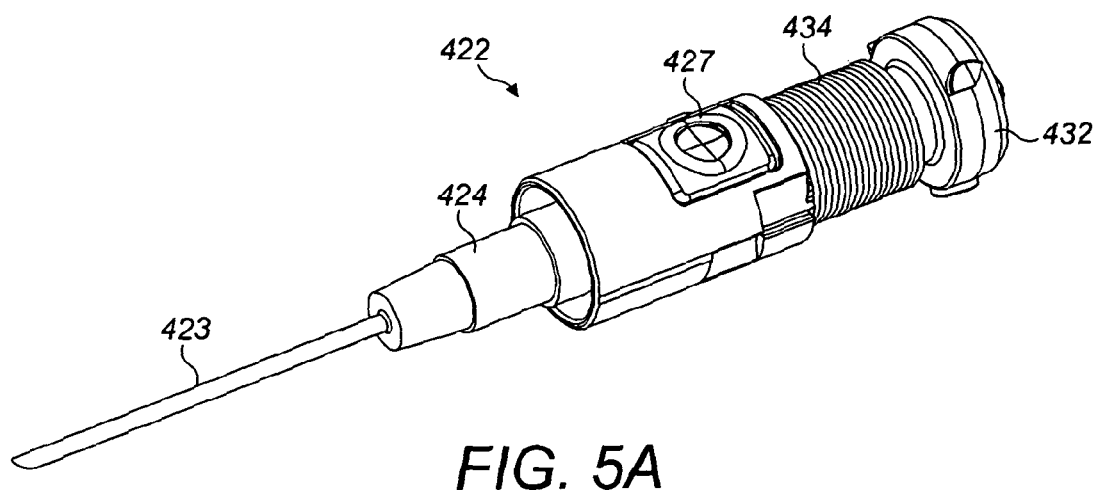
FIGS. 5A and 5B show perspective views of a carriage for use in a further alternative medical instrument of the present invention.
Figure 5B:
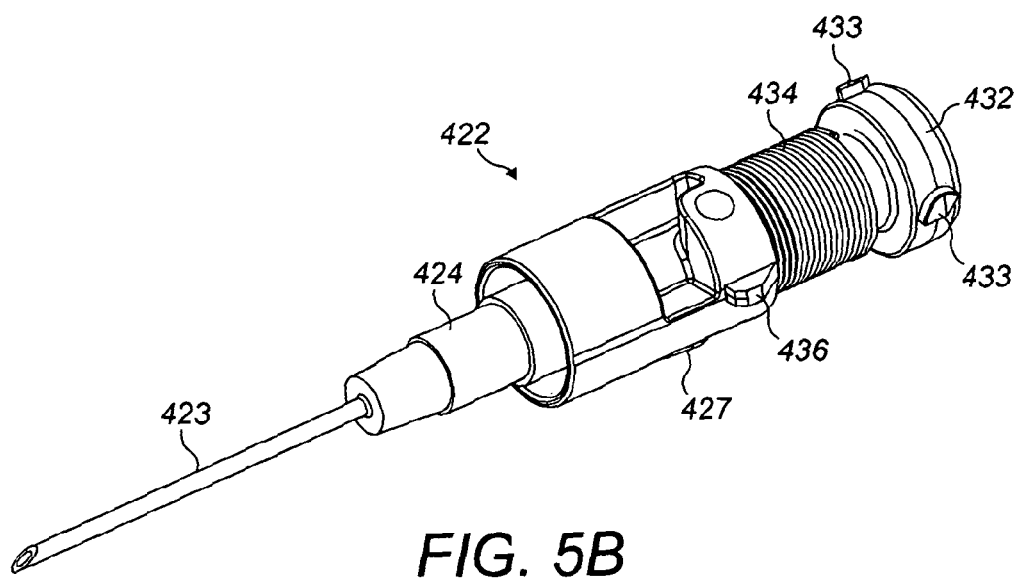

The carriage 422 has a substantially cylindrical body, as seen in FIGS. 5A and 5B. At its distal end is a connector 424 for a medical sharp, for example a standard Luer taper may be provided. A fluid channel 425 extends through the body from the distal end, first in an axial direction and then radially to a port 426 in the side wall of the body (FIG. 8A).

A valve 427 is attached to the body and closes the port 426. This may for example be a resilient diaphragm with a slit which is closed in a rest state. The slit will open if pressure on one side is increased.

As shown in FIG. 8A, when the retraction housing 412 is in its first position relative to the main housing 400 the passages 407, 413 are aligned with one another and also with the port 426 in the carriage 422. If fluid is present in the fluid chamber 409 in the main housing 400 and the plunger 408 is depressed, fluid will be forced through the passages 407, 413 and against the valve 427, causing it to open so that fluid can then pass through the carriage 422 to the needle 423 as shown by the arrows.

Conversely, if the plunger 408 is fully depressed so that nothing is present in the fluid chamber 409 and the plunger 408 is then withdrawn to open up the fluid chamber 409, the consequent reduction in pressure will open the valve 427 and allow fluid in the needle 423 to be withdrawn through the carriage 422 and passages 407, 413 into the fluid chamber 409.

In the first position of the retraction housing 412 relative to the main housing 400, a latch 428 retains the carriage 422 in a first position relative to the retraction housing 412. For ease of illustration the latch 428 is shown in FIGS. 8A and 8B as if it is located diametrically opposite to the passage 413 in the retraction housing 412. However, in practice the latch 428 may be at a different angular orientation to the passage 413. In this example, the passage 413 actually lies on plane 9:9' shown in FIG. 7D while the latch 428 lies on a plane 10:10'. The true cross section on line 9:9' is thus shown in FIGS. 9A-9D while the true cross section on line 10:10' is shown in FIGS. 10A-10D. FIGS. 8A-8B represent a section on line 8:8', i.e. which changes direction at the longitudinal axis of the retraction housing 412.

In this example, the latch 428 comprises a resilient arm 429 formed as part of the wall of the retraction housing 412. At rest the arm 429 bends radially outwardly (as in FIG. 8B). The free end of the arm 429 includes an enlarged head 430 which is engagable with a corresponding recess 431 in the carriage 422.

Figure 10A:
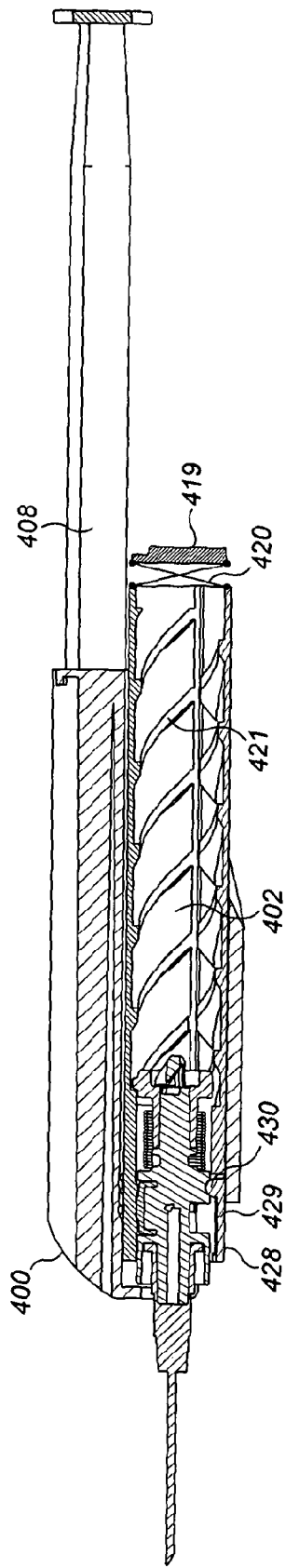
FIGS. 10A-10D show cross section views of the further alternative medical instrument at different stages of its operation taken about plane 10-10'.
Figure 10B:
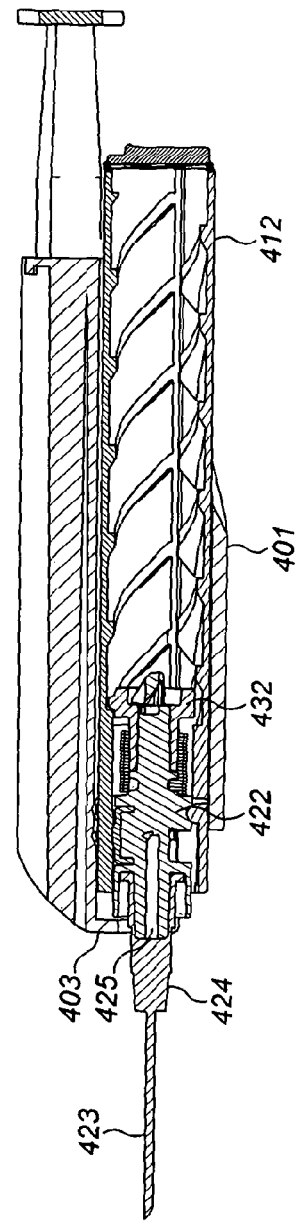
Figure 10C:
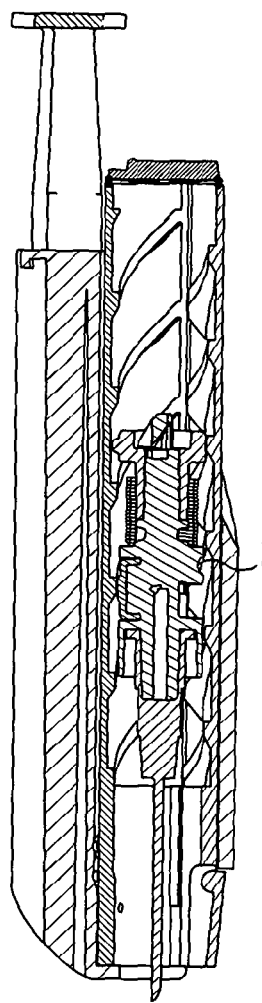
Figure 10D:
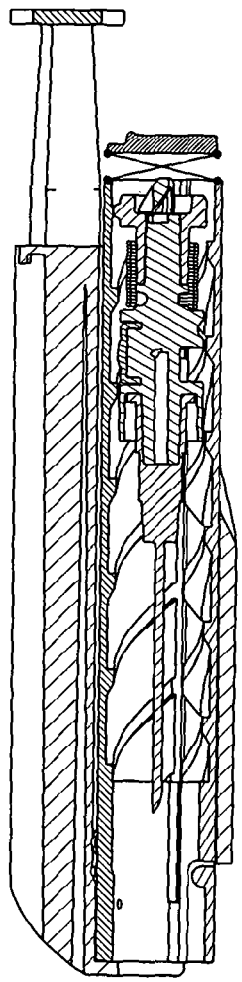

When the retraction housing 412 is in its first position relative to the main housing 400, the first curved wall 401 of the main housing 400 acts on the arm 429 in order to bias the head 430 into engagement with the recess 431, thereby retaining the carriage 422 in a fixed position relative to the retraction housing 412. This condition is shown in FIGS. 8A, 10A and 10B. When the retraction housing 412 is moved into its second position relative to the main housing 400, the arm 429 moves beyond the distal edge of the first curved wall 401 and is free to bend outwardly, coming out of engagement with the recess 431 in the carriage 422 (FIGS. 8B and 10C). The carriage 422 is then able to slide axially with respect to the retraction housing 412, although movement in a distal direction would be prevented by the lip 403 as shown in FIG. 8B.

A follower device 432 is rotatably attached to the proximal end of the carriage 422 and engaged with the helical path 421 in the retraction housing 412. In particular the follower comprises three equispaced radial projections 433 which engage with the three helices of the helical pathway 421. A stored energy device 434, typically a spring such as a torsion spring, is secured to the follower 432 and the carriage 422. When the retraction housing 412 is in its first position relative to the main housing 400, the stored energy device 434 tends not to unwind due to a combination of the friction between the follower projections 433 and the helical pathway and the fact that the carriage is retained by the latch 428. However, when the retraction housing 412 is moved to its second position relative to the main housing 400, and the carriage 422 is released, the stored energy device will unwind and this drives the follower device 432 proximally within the retraction housing 412. As the follower 432 is engaged with the helical path 421, the follower 432 rotates as it follows the path 421 under the action of the stored energy device 434.

The carriage 422 is connected to the follower 432 and stored energy device 434 and thus as the follower 432 moves proximally the carriage 422 is also retracted into the retraction housing 412. The interior surface of the retraction housing 412 also defines an axial pathway 435. Conveniently, this may be formed at the joint line between the two parts of the retraction housing 412. A projection 436 on the carriage 422 engages with the axial pathway 435 in order to prevent rotation of the carriage 422 in the retraction housing 412. Since the follower 432 is rotatable relative to the carriage 422, and the carriage itself prevented from rotation then as the follower 432 rotates along the helical path 421, the carriage 422 simply translates axially.

The typical sequence of operation is shown in FIGS. 9A-D. FIG. 9A shows the device ready for use as a syringe to deliver fluid, with a needle 423 attached to the carriage 422 and fluid in the fluid chamber 409. In FIG. 9B the plunger 408 has been fully depressed to deliver fluid though the passages 407, 413 and 425 to the needle 423. The actuating means 419 is depressed, forcing the retraction housing 412 distally. This releases carriage 422 which starts to retract into the retraction housing 412 under the action of the follower 432 and the stored energy device 434 as shown in FIG. 9C.

After retraction, the follower 432 and carriage 422 are located at the proximal end of the retraction housing 412 and the needle 423 is completely within the retraction housing 412 so that it is inaccessible and cannot cause injury. This is illustrated in FIG. 9D.

Use of the helical path 421 and follower 432 controls the rate at which the follower 432, carriage 422 and sharp 423 are withdrawn into the retraction housing 412. Thus, a smooth, non-jerky retraction is achieved. In the example shown the helical path 421 has a constant pitch. However, it is also possible to vary the pitch along its length in order to alter the retraction rate.

Controlled retraction also eliminates splutter, where droplets of fluid leak from the needle 432 as it is retracted. As noted above, when the retraction housing 412 is moved into its second position relative to the main housing 400, the proximal projection 414 of the locating means closes the passage 407 in the main housing 400. This seals the fluid chamber 409 in the main housing 400 to prevent any fluid leakage. At the same time the valve 427 closes and seals the port 426 in the carriage 422. Some fluid may remain in the fluid channel 425 formed in the carriage 422 and in the lumen of the needle 423. However, with the controlled retraction provided by the helical path 421, the forces acting on the fluid during retraction are insufficient to overcome the natural capillary action which tends to retain the fluid in the narrow channels of the carriage 422 and the needle 423. Therefore, fluid is not forced out of the needle 423 during retraction.

As described above, medical device 310 of this embodiment is in the form of a syringe which may be used either to deliver fluid into a patient or to aspirate fluid from a patient. As the skilled reader will appreciate, it is also possible that the main housing 400 consists only of the first curved wall 401 and first cylindrical passage 402, i.e. it is in the form of a cylindrical collar into which the retraction housing 412 may be fitted. The collar may include a port for connection to a fluid delivery or collection device in a similar manner to that shown in FIGS. 4A and 4B. However, if the medical device is intended for providing a sharp simply for forming a puncture and is not required to provide a fluid pathway, then the collar need not include such a port.

In this way, a versatile medical device is provided which can be used with a needle or other medical sharp and which provides for automatic controlled retraction and safe retention of the sharp after use. The device can provide for fluid delivery or aspiration and the controlled retraction and closure of the fluid channels in the device prevents leakage of fluid and associated contamination risks. Different sharps, for example different sized needles, may be used with the device due to the inclusion of a standard fitting such as a Luer taper. The sharp can be retracted at any time as required by the user and it is not necessary for the plunger to be fully depressed or withdrawn before the retraction mechanism is operated. The user can therefore chose not to deliver all of the fluid in the chamber, or when to stop aspirating fluid. The risk of inadvertent actuation is minimised by the flexible connection between the actuation means and the retraction housing. The main housing containing the fluid chamber is separable from the retraction housing. Thus, the chamber may be pre-filled with a medicament for delivery before fitting of the retraction housing and the sharp, or the housing with the chamber full of aspirated fluid may be removed for processing whilst the retraction housing and sharp are disposed of safely.

It will be appreciated that a number of variations and modifications can be made to the invention without departing from the scope of the claims.

The invention claimed is:

1. A medical device comprising
an outer housing having a first wall defining a first passage with proximal and distal ends,
a retraction housing slidably received in the first passage, the retraction housing having proximal and distal ends and a wall with an interior surface wall defining a helical path,
a carriage for releasably receiving a medical sharp, the carriage slidably received in the distal end of the retraction housing,
latch means for retaining the carriage in a first position in the retraction housing,
a follower connected to the carriage and engaged with the helical path,
a stored energy device connected to the follower and the carriage, wherein the medical device is characterized by the outer housing, and
actuation means operable to move the retraction housing towards the distal end of the first passage, thereby to release the latch means such that the stored energy device is operable to drive the follower along the helical path and to retract the carriage towards the proximal end of the retraction housing.

2. A medical device as claimed in claim 1, further comprising locating means operable to retain the retraction housing relative to the outer housing in a first position and in a second position, wherein the actuation means is operable to move the retraction housing from the first position to the second position.

3. A medical device as claimed in claim 2, wherein the locating means comprises at least one projection on one of the outer housing and the retraction housing and at least two corresponding recesses to receive the projection on the other of the outer housing and the retraction housing.

4. A medical device as claimed in claim 2, further comprising a latch to retain the carriage in a first position relative to the retraction housing, wherein the actuation means is operable to release the latch such that relative movement between the carriage and the retraction housing is permitted.

5. A medical device as claimed in claim 4, wherein the latch comprises a resilient member on one of the retraction housing and the carriage and biased into engagement with the other of the retraction housing and the carriage when the retraction housing is in its first position relative to the outer housing and wherein the latch is disengaged when the retraction housing is moved into its second position relative to the outer housing.

6. A medical device as claimed in claim 1, wherein the outer housing comprises a stop to limit distal movement of the retraction housing and the carriage in the first passage.

7. A medical device as claimed in claim 1, further comprising a fluid channel extending through the carriage from a distal end to a side surface thereof, and the retraction housing wall comprises a port,
wherein when the retraction housing is located in its first position relative to the outer housing, the port in the retraction housing communicates with the fluid channel in the carriage.

8. A medical device as claimed in claim 7, further comprising valve means on the carriage to close the fluid channel where it exits the side wall of the sharp connector.

9. A medical device as claimed in claim 1, wherein the outer housing further comprises a second wall defining a second passage adjacent to the first passage, the second passage having a closed distal end and an open proximal end, a port formed through the outer housing adjacent the closed distal end of the second passage which communicates with the port in the retraction housing when the retraction housing is in the first position relative to the outer housing, and a plunger slidably received in the second passage to form a chamber for fluid between the plunger and the distal end of the second passage.

10. A medical device as claimed in claim 9, wherein when the retraction housing is located in its second position relative to the outer housing:
the port in the retraction housing does not communicate with the port in the outer housing; and
the wall of the retraction housing blocks the port in the outer housing.

11. A medical device as claimed in claim 1, wherein the stored energy device comprises spring means.

12. A medical device as claimed in claim 1, wherein the follower is rotatable relative to the carriage and the carriage is precluded from rotation in the retraction housing, such that as the follower is driven along the helical path, the carriage moves axially but does not rotate.

13. A medical device as claimed in claim 1, wherein the actuation means comprises a body connected to the proximal end of the retraction housing by at least one flexible arm.

* * * * *